(12) United States Patent  (10) Patent No.: US 6,702,807 B2
Peyman                     (45) Date of Patent:     Mar. 9, 2004

(54) ABLATABLE INTRACORNEAL INLAY WITH PREDETERMINED REFRACTIVE PROPERTIES

(75) Inventor: Gholam A. Peyman, New Orleans, LA (US)

(73) Assignee: Minu, L.L.C., Pittsboro, NC (US)

( * ) Notice: Subject to any disclaimer, the term of this patent is extended or adjusted under 35 U.S.C. 154(b) by 248 days.

(21) Appl. No.: 09/949,085

(22) Filed: Sep. 10, 2001

(65) Prior Publication Data

US 2003/0093066 A1 May 15, 2003

(51) Int. Cl.⁷ .................................................. A61F 9/007
(52) U.S. Cl. ................................ 606/5; 606/4; 128/898
(58) Field of Search ........................... 606/4–5; 128/898

(56) References Cited

U.S. PATENT DOCUMENTS

| 4,655,774 | A | 4/1987 | Choyce | 623/5 |
| 4,840,175 | A | 6/1989 | Peyman | 128/303.1 |
| 5,196,027 | A | 3/1993 | Thompson et al. | 623/5 |
| 5,405,384 | A | 4/1995 | Silvestrini | 623/5 |
| 5,722,971 | A | 3/1998 | Peyman | 606/5 |
| 5,725,575 | A * | 3/1998 | O'Donnell, Jr. | 606/4 |
| 5,919,185 | A | 7/1999 | Peyman | 606/5 |
| 6,063,073 | A | 5/2000 | Peyman | |
| 6,102,946 | A | 8/2000 | Nigam | 623/5 |
| 6,197,019 | B1 | 3/2001 | Peyman | |
| 6,264,648 | B1 * | 7/2001 | Peyman | 606/5 |
| 6,280,470 | B1 | 8/2001 | Peyman | |
| 2001/0034516 | A1 * | 10/2001 | Peyman | 606/5 |

* cited by examiner

Primary Examiner—Roy D. Gibson
Assistant Examiner—Henry M. Johnson, III
(74) Attorney, Agent, or Firm—Roylance, Abrams, Berdo & Goodman, LLP (57) ABSTRACT

A method of correcting the refractive error in a cornea of an eye, including forming a flap in the surface of the cornea, and moving the flap to expose first and second internal surfaces of the cornea. An implant is positioned adjacent the first internal surface, at least a portion of the implant having refractive properties and held adjacent the first internal surface using a tool. At least a portion of the implant is ablated with a light emitting device, when the implant is positioned on the first exposed surface of the cornea and being held by the instrument. The flap is then repositioned over the implant.

37 Claims, 7 Drawing Sheets

ABLATABLE INTRACORNEAL INLAY WITH PREDETERMINED REFRACTIVE PROPERTIES

CROSS-REFERENCE TO RELATED APPLICATION

Related subject matter is described in U.S. application Ser. No. 09/758,263, filed Jan. 12, 2001, the entire contents of which is herein incorporated by reference.

BACKGROUND OF THE INVENTION

1. Field of the Invention

The present invention relates to a system and method for modifying the refractive error in the live cornea of an eye. More particularly, the present invention relates to a system and method for modifying the live cornea by separating an internal area of the live cornea into first and second opposed internal surfaces, forming a corneal flap, positioning an implant having a predetermined refractive portion on one of the internal surfaces and holding the implant adjacent thereto using a ring-shaped instrument, and then ablating the implant using a light emitting device and replacing the corneal flap over the ablated implant.

2. Description of the Related Art

A conventional method for correcting the refractive error in a cornea is known as keratophakia, which involves implantation of a lens inside the cornea. Keratophakia uses an implant, which is placed into the cornea approximately equidistant from the exterior surface of the cornea and the interior surface. The procedure is usually done by first preparing a lens from corneal donor tissue or from synthetic material using a cryo-lathe. The lens is implanted by removing a portion of the cornea with a device called a microkeratomes, and the tissue is sutured back into place over the lens. However, there can be problems when microkeratomies are used for cutting the cornea. First, irregular keratectomies or perforations of the eye can result. Second, the recovery of vision can be rather prolonged.

Another surgical technique exists that uses a femtosecond laser to separate layers inside the stromal at least two-thirds of the distance from the top surface of the cornea to the inside of the eye. An incision is made to access this area, and a solid inlay is inserted to help correct myopia in the eye. However, separating the layers in the bottom two-thirds of the stromal makes it difficult to access the separated area to insert the inlay, and virtually impossible to change or modify the inlay without another extensive surgical procedure. This procedure also requires making an incision, which is parallel to the visual axis and is limited in the lateral direction by a maximum size of 0.3 mm to encase a relatively rigid inlay that forces the tissue in the lateral direction.

A further surgical technique exists that forms a flap-like portion of the live cornea, which is removed to expose an inner surface of the cornea. A blank is positioned on the exposed inner surface of the cornea, and a laser beam is then directed onto certain portions of the blank based on the type of ametropic condition (i.e., myopia, hyperopia or astigmatism) of the eye, so that the laser beam ablates those portions and thus reshapes the blank. The laser beam can also be directed onto certain portions of the exposed surface of the cornea to ablate those surfaces of the cornea. The flap-like portion of the cornea is repositioned over the remaining portion of the blank, so that the remaining portion of the blank influences the shape of the reattached flap-like portion of the cornea and thus modifies the curvature of the cornea. A more detailed description of this procedure is described in U.S. Pat. No. 5,919,185 to Peyman, the content of which is herein incorporated by reference.

Although this technique is very successful, this type of procedure may require ablation of a large portion of the blank, which results in the dispersion of a relatively large amount of heat. This heat can cause the lens to shrink and thus possibly inadvertently alter the intended refractive properties of the cornea, in which event correction will be less than desired or even irregular.

Additional surgical techniques exist that use ultraviolet light and short wavelength lasers to modify the shape of the cornea. For example, excimer lasers, such as those described in U.S. Pat. No. 4,840,175 to Peyman, the entire content of which is incorporated by reference herein, emit pulsed ultraviolet radiation that can be used to decompose or photoablate tissue in the live cornea to reshape the cornea. This technique is commonly known as the laser surgical technique known as laser in situ keratomycosis (LASIK).

In the LASIK technique, a portion of the front of the live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is reattached over the ablated portion of the cornea and assumes a shape substantially conforming to that of the ablated portion.

However, because only certain amount of cornea can be ablated without the remaining cornea becoming unstable or experiencing outbulging (eklasisa), this technique is not especially effective in correcting very high myopia. That is, a typical cornea is on average about 500 microns thick. The laser ablation technique requires that at least about 250 microns of the corneal stroma remain after the ablation is completed so that instability and outbulging do not occur.

Additional methods for correcting the refractive error in the eye include inserting an implant in-between layers of the cornea. Generally, this is achieved using several different methods. One method involves inserting a ring between layers of the cornea, as described in U.S. Pat. No. 5,405,384 to Silvestrini. Typically, a dissector is inserted in the cornea and forms a channel therein. Once it is removed, a ring is then inserted into the channel to alter the curvature of the cornea. In another method, a flap can be created similarly to the LASIK procedure and a lens can be inserted under the flap, as described in U.S. Pat. No. 5,722,971 to Peyman. A further method involves forming a pocket using an instrument, and inserting an implant into the pocket, as described in U.S. Pat. No. 4,655,774 to Choyce. The entire contents of each of these three patents are incorporated herein by reference.

However, with the above-described techniques, a knife or other mechanical instrument is generally used to form the channel, flap or pocket. Use of these instruments may result in damage or imprecision in the cut or formation of the desired area in which the implant is placed.

Therefore, there exists a need for an improved method of correcting refractive error in the cornea of an eye.

SUMMARY OF THE INVENTION

Accordingly, a primary object of the present invention is to provide a method for modifying the cornea of an eye without experiencing the drawbacks associated with the known techniques discussed above, to thus correct severe ametropic conditions.

A further object of the present invention is to provide a method for modifying the cornea of an eye by using a device that can be placed on the surface of the live cornea and reshaped thereon.

Still a further object of the present invention is to provide a method for modifying the cornea of an eye by removing a layer of the live cornea to expose a surface underneath, then placing an implant with predetermined refractive properties on the exposed surface, which can be reshaped while on the exposed surface.

Yet another object of the present invention is to provide a method for modifying the cornea of an eye wherein the implant can be held adjacent to the exposed surface of the cornea using an instrument during ablation thereof.

Yet another object of the present invention is to provide a method for modifying the cornea of an eye that allows for corrective measures that avoid or eliminate outbulging or instability in the cornea.

The foregoing and other objects are substantially attained by a method of correcting the refractive error in a cornea of an eye, including the steps of forming a flap in the surface of the cornea, moving the flap to expose first and second internal surfaces of the cornea, positioning an implant adjacent the first internal surface, with at least a portion of the implant having refractive properties, holding the implant adjacent the first internal surface using a tool, ablating at least a portion of said implant with a light emitting device when said implant is held in place by the tool on the first exposed surface of the cornea, and repositioning the flap over the implant.

The foregoing objects of the present invention are further attained by a method of correcting the refractive error in a cornea of an eye, including the steps of separating a portion of the surface of the cornea into first and second internal surfaces to form a corneal layer, the first surface facing in an anterior direction of the eye and the second surface facing in a posterior direction of the eye, moving the corneal layer to expose the first internal surface, positioning a lens on the first internal surface, holding the lens stationary relative to the first internal surface using an instrument, ablating at least a portion of the lens using a laser when said lens is being held by said instrument, and moving the corneal layer so that the second internal surface substantially overlies the lens.

Other objects, advantages, and novel salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE PREFERRED EMBODIMENT

Figure 1:
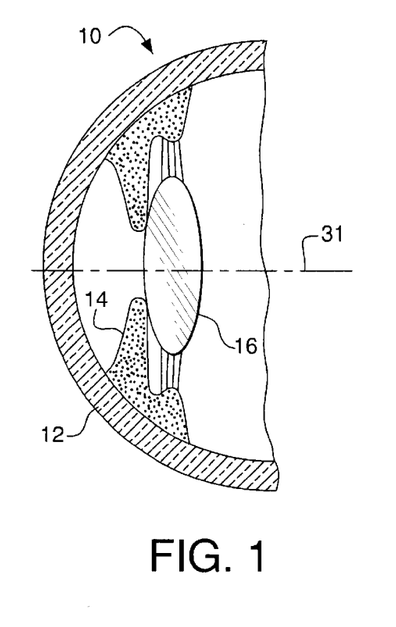
FIG. 1 is a side cross-sectional view in section taken through the center of an eye showing the cornea, pupil and lens.

FIG. 1 is a side cross-sectional view taken through the center of an eye 10, which includes a cornea 12, a pupil 14 and a lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

As seen in FIGS. 1–10, the refractive properties of eye 10 can be altered by forming a flap 18 in the cornea 12 and then placing lens or implant 20 having a predetermined refractive portion under flap 18. Implant 20 can be held adjacent the exposed surface of the eye using tool or instrument 22, allowing the implant to be easily shaped using a laser 24 to ablate a portion 26 of the implant 20.

To begin, the refractive error in the eye is measured using wavefront technology, as is known to one of ordinary skill in the art. A more complete description of wavefront technology is disclosed in U.S. Pat. No. 6,086,204 to Magnate, the entire content of which is incorporated herein by reference. The refractive error measurements are used to determine the appropriate lens or implant 20 to best correct the error in the patient's cornea. Preferably, the lens 20 is manufactured or shaped prior to the use of the wavefront technology and is stored in a sterilized manner until that specific lens shape or size is needed. However, the information received during the measurements from the wavefront technology can be used to form the lens using a cryo-lathe, or any other desired system or machine.

Figure 2:
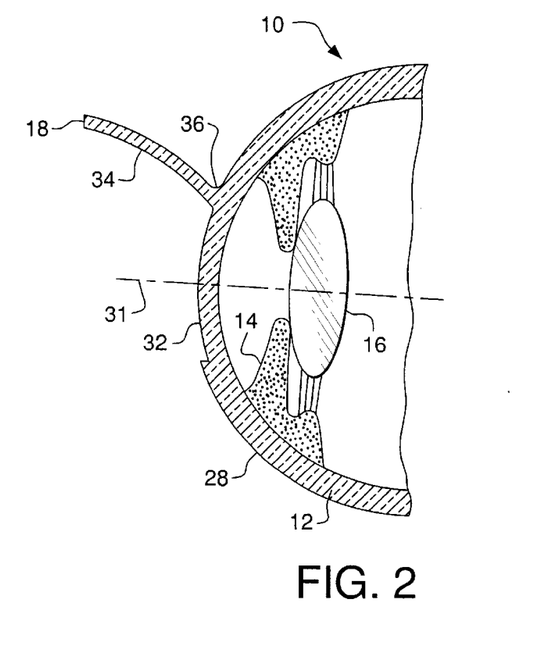
FIG. 2 is a side cross-sectional view in section of the eye of FIG. 1 with a flap formed in the surface of the cornea.

A flap or portion 18 can be formed in the surface 28 of the cornea 12, as seen in FIG. 2. The flap may be formed be any means desired, such as with a knife, microkertome, or with a laser. Preferably an internal area of the cornea is separated into first 32 and second 34 substantially circular shaped internal surfaces to form the circular shaped corneal flap 18. First internal surface 32 faces in an anterior direction of cornea 12 and the second internal surface 34 faces in a posterior direction of the cornea 12. The flap 18 preferably has a uniform thickness of about 10–250 microns, and more preferably about 80–100 microns, but can be any suitable thickness. A portion 36 of flap 18 preferably remains attached to the cornea by an area at the periphery 30 of the flap. However, the flap can be any suitable configuration, such as a flap attached to the cornea at a location other than at the periphery or a flap that is not attached to the cornea at all. Additionally, the flap may be shaped or sized as desired and does not need to be circular.

The flap is moved or rotated about portion 36 using any device known in the art, such as spatula or microforceps or any other device, to expose the first and second corneal surfaces 32 and 34, respectively. The flap preferably exposes a portion of the corneal surface 32 that intersects the main optical axis 31 and allows uninhibited access thereto.

Implant 20 can then be positioned adjacent the surface 32 of the cornea. Implant 20 is preferably any polymer or hydrogel having about 50% water content; however, the water content can be any percentage desired. The lens may be formed from synthetic or organic material or a combination thereof. For example, the lens can be collagen combined with or without cells; a mixture of synthetic material and corneal stromal cells; silicone or silicone mixed with collagen; methylmetacrylate; any transparent material, such as polyprolidine, polyvinylpylidine, polyethylenoxyde, etc.; or any deformable polymer, which can change its shape with radiation after implantation.

Figure 3:
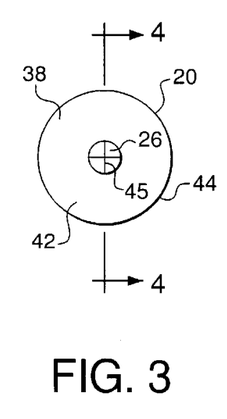
FIG. 3 is a top view of an embodiment of an implant according to an embodiment of the present invention.
Figure 4:
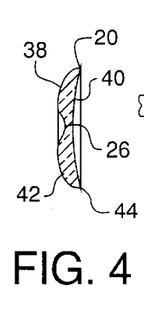
FIG. 4 is a side cross-sectional view of the implant of FIG. 3 taken along lines 4—4.

Additionally, implant 20 has a first side or surface 38 and a second side or surface 40 and is preferably a concave shape (so that at least a portion of the implant has a refractive portion) for correcting myopia, as seen in FIGS. 3 and 4. Second surface 40 preferably is curved and pliable, so that it is able to conform to the first surface 32 of the cornea 12. The implant is preferably substantially circular, having a diameter of between about 2–10 mm and has a curved bump 42 at the periphery of the implant. The bump extends from the outer edge 44 of the implant and increases thickness from the outer edge toward the center of the implant. The maximum thickness of the bump is between about 10–400 microns thick, but can have any suitable thickness. The bump decreases in thickness as it approached the center of the implant, where the recessed portion 26 is defined. Recessed portion 26 preferably has a marker 45, such as cross hairs thereon. The marker can be used to help center the implant on the exposed surface of the eye, or for indication of where to aim a laser, as described below. Recessed portion 26 is a substantially circular relatively thin membrane that extends about the center of the implant. The recessed portion 26 is preferably between about 1–200 microns thick. It is noted that the dimensions and shape of the implant and its features, such as the bump, recessed portion and so on are preferable, and the implant and is corresponding features can be of any shape or size desired. However, for various reasons, the eye may not be corrected to the desired amount using a lens having a predetermined or stock refractive power.

Figure 5:
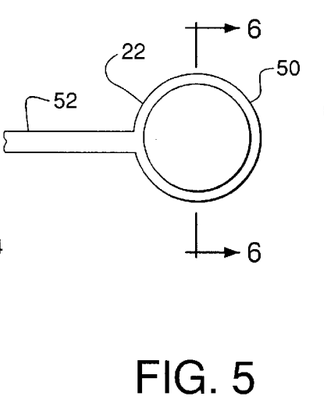
FIG. 5 is a top view of an instrument adapted to hold the implant of FIG. 3 adjacent the surface of the cornea according to an embodiment of the present invention.
Figure 6:
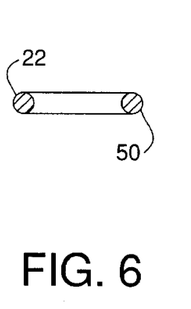
FIG. 6 is a side cross-sectional view of the instrument of FIG. 5 taken along lines 6—6.
Figure 7:
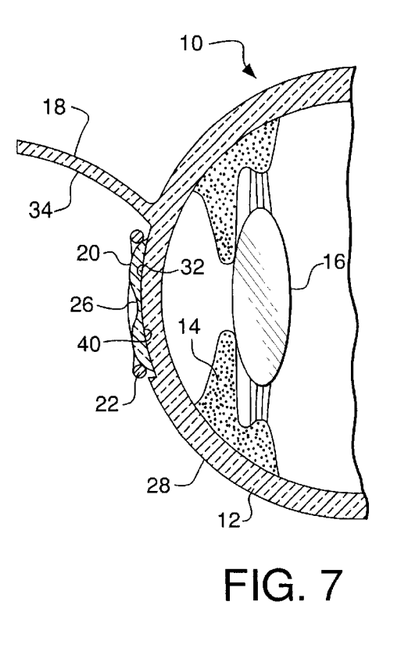
FIG. 7 is a side cross-sectional view in section of the eye of FIG. 2 with the implant of FIG. 4 held adjacent the exposed surface of the cornea using the instrument of FIG. 6.

As seen in FIGS. 5–7, a substantially ring shaped tool or instrument 22 is preferably used to hold implant 20 adjacent or on the exposed surface of the cornea. Instrument 22 is preferably a resilient material, such as metal, surgical steel, or plastic. The instrument has a head 50 and a handle 52. The thickness of the head is preferably between about 0.1 to 3 mm; however, the head, as well as the handle, can be any size and shape desired. The head and the handle can be unitary and formed from the same mold or piece of material, or the handle can be permanently affixed to the head by any conventional method. Additionally, the handle 52 can be removable attached to the head 50 by any means desired, such as external threads on the handle and internal threads in the head. By having the handle removably attached to the head, different sized heads could be used to grasp an implant using the same handle. This would be beneficial if it were necessary to hold the periphery of different diameter implants.

Furthermore, the instrument 22 can be used to press and hold the implant 20 against the first internal surface 32 or it can be used to frictionally hold the implant, with the implant extending through the opening of the instrument and adjacent or on the first surface 32. By holding the instrument and implant as described, the implant can be stabilized in front of the eye for more effective and accurate ablation. Instrument 22 does not necessarily need to be ring-shaped, and can be any shape and size that would allow the implant to be held adjacent or on either of the first or second internal surfaces 32 and 34.

Once positioned on the exposed surface 32 of the cornea 12, the shape of the implant can be further modified sufficiently to influence the shape of the flap-like layer 18 and to thus change the refractive power of the flap-like layer sufficiently to correct the abnormality of the eye 10. Generally, every 10 micron change in curvature of the cornea will change the refractive power of the cornea by 1 diopter.

Figure 8:
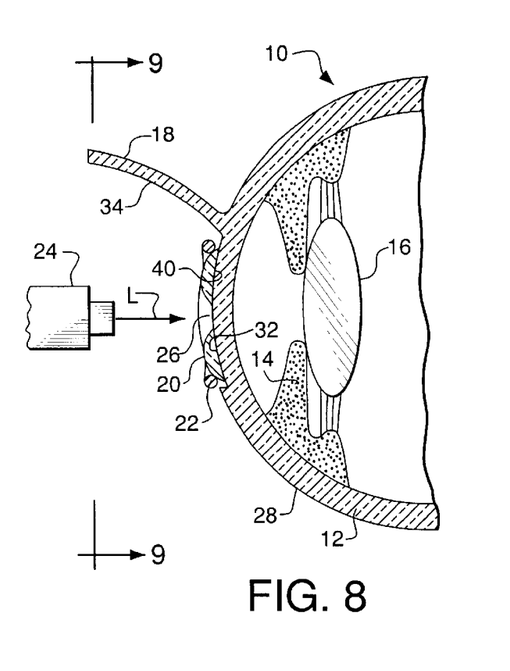
FIG. 8 is a side cross-sectional view of the implant and eye of FIG. 7 with a laser ablating a portion of the implant.

As shown in FIG. 8, the implant is preferably modified by directing a laser beam L at the first surface of the implant 20 that is opposite to the second surface of the implant 20 that is supported on the exposed surface 32 of the cornea 12. The laser beam L can be emitted from any type of laser 24 typically used in eye surgery methods, such as an excimer laser 24 or the like as described in U.S. Pat. No. 4,840,175 referenced above. Using the cross hairs shown in FIG. 3, the laser beam can be accurately directed onto the surface of the lens.

Additionally, in instances where a nonuniform area of the implant needs to be ablated, the marker allows easier identification and ablation of this type of area. In other words, if it is necessary to ablate a portion of the lens that is not concentric with the main optical axis of the eye, for prezbiopia or astigmatic correction, the marker can be used to allow the laser beam to be properly aligned.

As shown in FIG. 8, the laser beam L will begin to ablate or erode an area 26 of the implant to which the laser beam is directed. The area of the implant to which the laser beam L is directed and which is ablated is selected to remedy a specific type of abnormality from which the eye is suffering.

Figure 9:
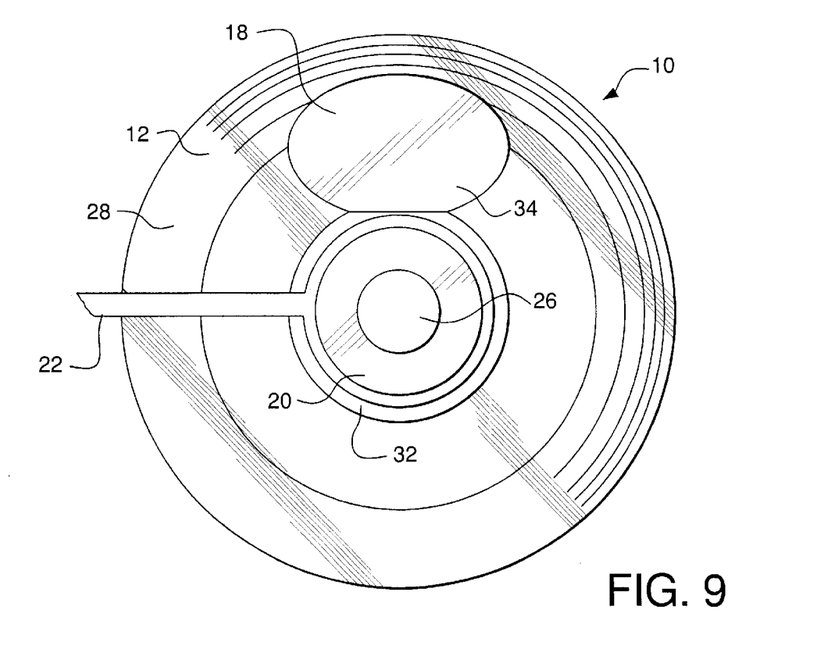
FIG. 9 is a front elevational view of the implant and eye of FIG. 8 taken along lines 9—9.

For example, if the implant is being ablated to further correct a myopic condition beyond the correction of the refractive portion of the eye, the laser beam L will be directed toward a central area of the implant so as to ablate that central area. As shown in FIGS. 8 and 9, for example, the implant 20 is disk-shaped, and the area that is ablated is preferably substantially circular. Of course, the shape of the ablated area can be any desired shape necessary to effect correction of a particular abnormality of the eye.

Preferably, the implant is made of a material that will absorb all or substantially all light having a wavelength within the laser light spectrum. Therefore, when the laser beam L is irradiated onto the implant 20, none or substantially none of the laser beam will pass through the implant 20 to ablate any portion of the cornea 12. However, the material of the implant 20 will allow all or substantially all light having a wavelength within the visible light spectrum to pass therethrough.

Hence, the laser beam L can be directed to the implant 20 until the ablated central area becomes a hole with a frusto-conical wall which passes entirely through the implant 20 to expose a portion of the surface 32 of the cornea 12. As noted, the area 26 is only between about 1–200 microns and therefore the ablated portion is preferably relatively small. Also, it is not necessary to completely ablate this area and only a portion therefore can be ablated. Of course, the hole can have a cylindrically or substantially cylindrically shaped wall, or any other shape as would be formed by the laser beam L. As shown in FIG. 8, none or essentially none of the surface 32 of the cornea has been ablated by the laser beam.

Figure 10:
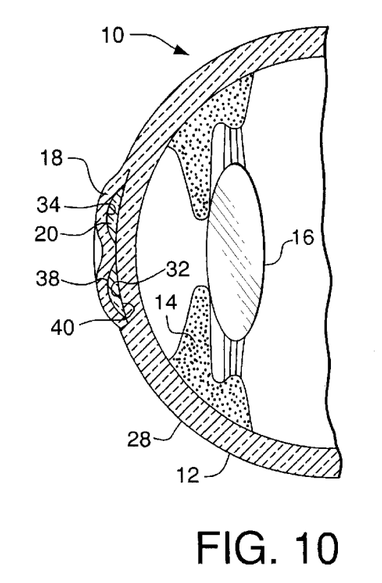
FIG. 10 is a side cross-sectional view of the implant and eye of FIG. 9 with the flap repositioned over the ablated implant.
Figure 11:
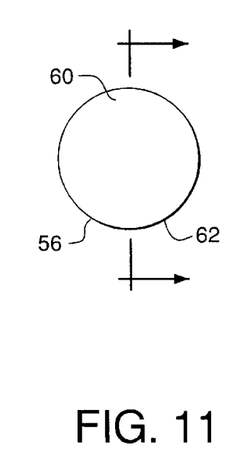
FIG. 11 is a top view of an implant according to another embodiment of the present invention.
Figure 12:
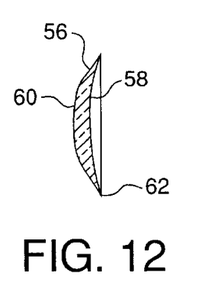
FIG. 12 is a side cross-sectional view of the implant of FIG. 11 taken along lines 12—12.

The flap 18 is then replaced so that it covers or lies over the implant in a relaxed state, as seen in FIG. 10. In other words, implant 20 does not force flap 18 away from the internal surface 32 and therefore the refractive properties of the cornea are not altered due to a tension force being applied to the flap.

Figure 13:
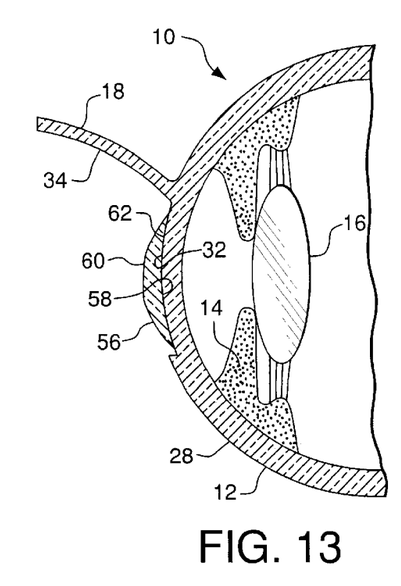
FIG. 13 is a side cross-sectional view in section of the eye of FIG. 2 with the implant of FIG. 11 positioned adjacent the exposed surface of the cornea.

Furthermore, different types of implants may be used to help correct additional types of vision problems. For example, as shown in FIGS. 11–15, a convex lens or implant 56 can be used to correct hyperopic error. As seen specifically in FIGS. 11 and 12, implant 56 is preferably a substantially circular inlay having a first side or surface 58 and a second side or surface 60. Implant 56 has a diameter of about 1–9 mm and a thickness of between about 10–200 microns. Additionally, each surface of the implant preferably has a predetermined curvature and the implant material is preferably pliable, as described above, which allows the implant to match the curvature of the exposed surface of the cornea, as seen in FIG. 13, and also results in a predetermined refractive property that corrects much of the hyperopic refractive error in the eye. However, for various reasons, the eye may not be corrected to the desired amount using a lens having a predetermined or stock refractive power.

Figure 14:
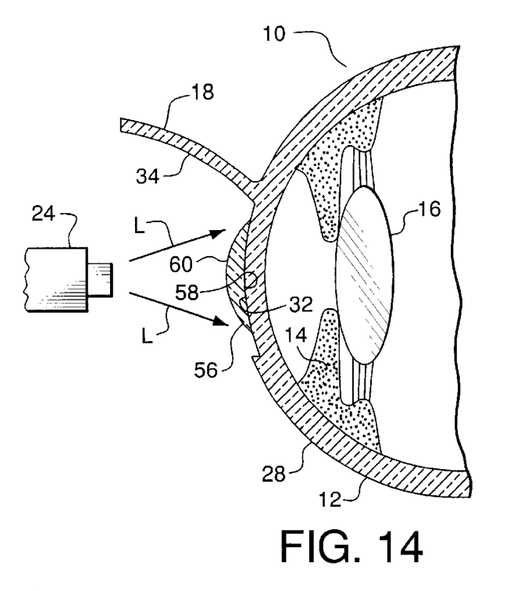
FIG. 14 is a side cross-sectional view of the implant and eye of FIG. 13 with a laser ablating a portion of the implant.

As described above, wavefront technology can be used to determine precisely the refractive error of a specific eye. This information can be used to program a system, which would activate an excimer laser 24, thereby ablating a peripheral portion 62 of the implant 56, as seen in FIG. 14. As stated above, only a thickness of between about 1–200 microns would need to be ablated to further correct the refractive error in the eye.

Figure 15:
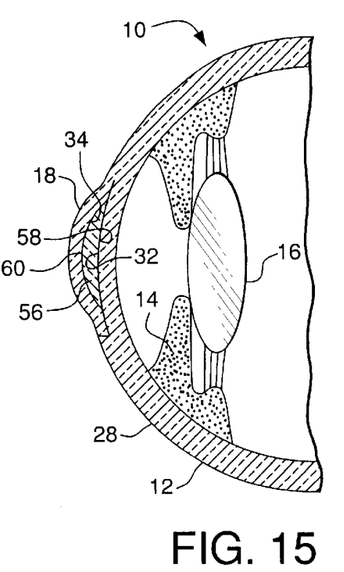
FIG. 15 is a side cross-sectional view of the implant and eye of FIG. 14 with the flap repositioned over the ablated implant.
Figure 16:
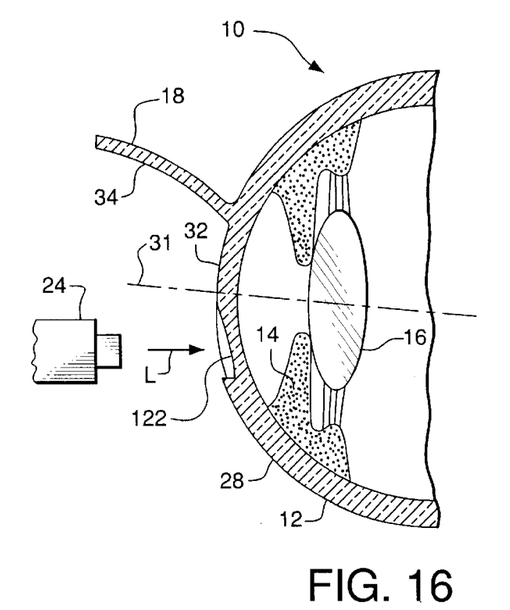
FIG. 16 is a side cross-sectional view of an eye wherein the exposed surface of the cornea of the eye is ablated prior to positioning an implant thereon according to a further embodiment of the present invention.

Flap 18 can then be repositioned over the exposed surface and the implant 56 in a relaxed state, as shown in FIG. 15, and similar to the repositioning of the flap described above.

It should be noted that any discussion of the above concave implant 20 can and does apply to the implant 56. For example, lens 56 is generally positioned and ablated in a similar manner and implant 56 can have a similar marker, such as cross hairs, as implant 20.

When correcting either implant with the excimer laser, it is possible to simultaneously use wavefront technology or adoptic optic technology to create a near perfect correction in the eye and to remove all corneal irregularities. By using this technique to correct vision, it is possible to achieve 20/10 vision in the patient's eye or better.

Furthermore, at the end of the procedure topical agents, such as an anti-inflammatory, antibiotics and/or an antiprolifrative agent, such as mitomycin or thiotepa, at very low concentrations can be used over the ablated area to prevent subsequent haze formation. The mitomycin concentration is preferably about 0.005–0.05% and more preferably about 0.02%. A short-term bandage contact lens may also be used to protect the cornea.

By forming prerefractive implants, only small a portion of the implant need be ablated, simplifying the type of polymer required. For example, as described above the polymer does not have to tolerate as much heat as an implant that is not prerefractive, thus reducing the likelihood that the implant will change shape.

Embodiment of FIGS. 16–19

As shown in FIGS. 16–19, in the case of astigmatic refractive error, the exposed surface of the cornea, preferably the stroma can be ablated to correct the refractive error in the eye. For example, as shown specifically in FIG. 16, a portion 122 offset from the main optical axis 31 of the eye can be ablated to correct an astigmatic problem.

Figure 17:
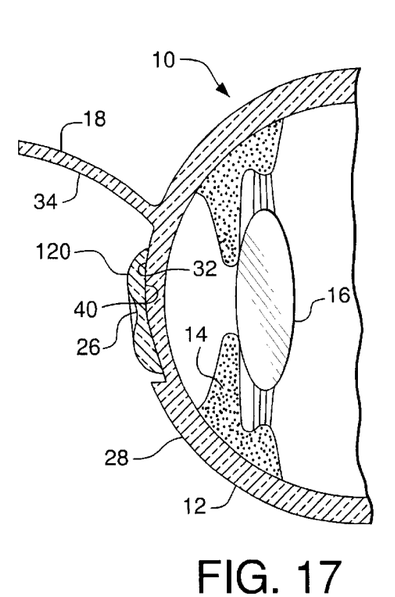
FIG. 17 is a side cross-sectional view in section of the eye of FIG. 16 with an implant positioned adjacent the exposed surface of the cornea.
Figure 18:
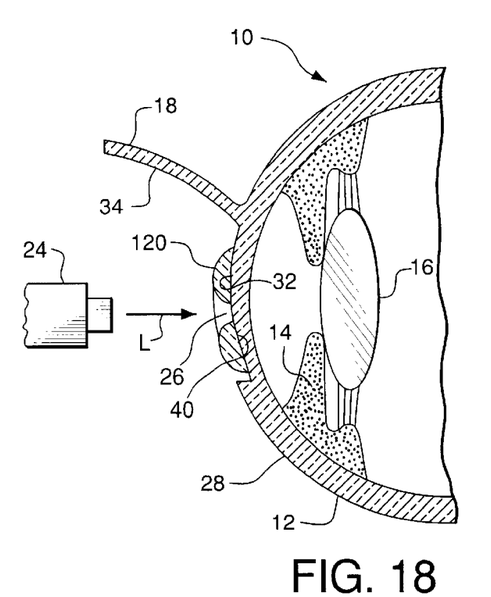
FIG. 18 is a side cross-sectional view in section of the implant and eye of FIG. 17 with a laser ablating a portion of the implant.

As described above, the refractive error in the eye is measured using wavefront technology. A flap 18 is then formed in the surface of the cornea and a portion of the exposed surface is ablated. As shown in FIG. 17, an implant or lens 120 can then be positioned as described above. Preferably, implant 120 has predetermined refractive properties for myopic or hyperopic or astigmatic correction. Implant 120 can be substantially similar to implant 20 or implant 56 or any other desired shape. Furthermore, as seen in FIG. 18, lens 120 can be ablated in any manner desired to further correct myopic, hyperopic or astigmatic error in the eye, as described above.

Figure 19:
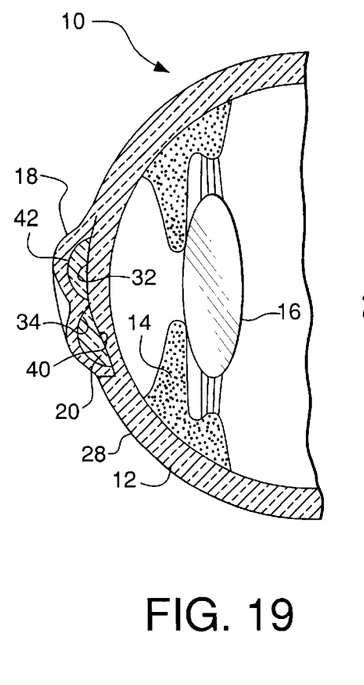
FIG. 19 is a side cross-sectional view of the implant and eye of FIG. 18 with the flap repositioned over the ablated implant.
Figure 20:
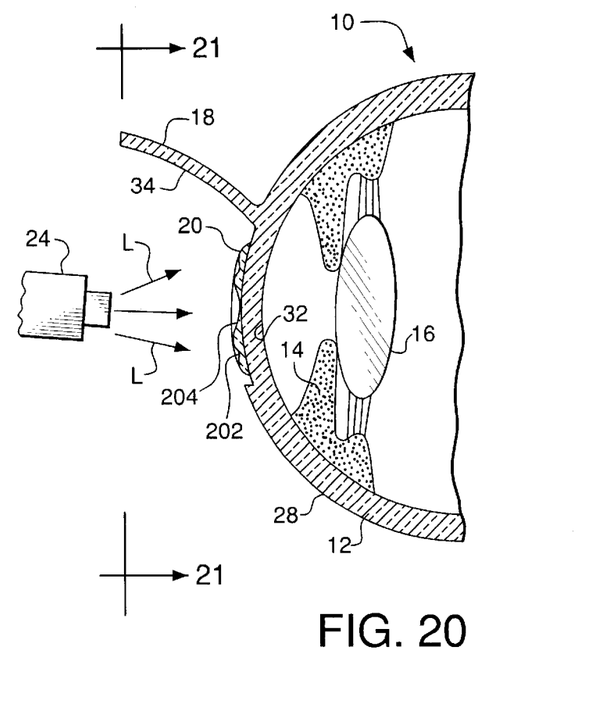
FIG. 20 is a side cross-sectional view of the eye of FIG. 2 with the implant of FIG. 4 placed adjacent thereto and being laser ablated into separate zones for correction of near and far vision.
Figure 21:
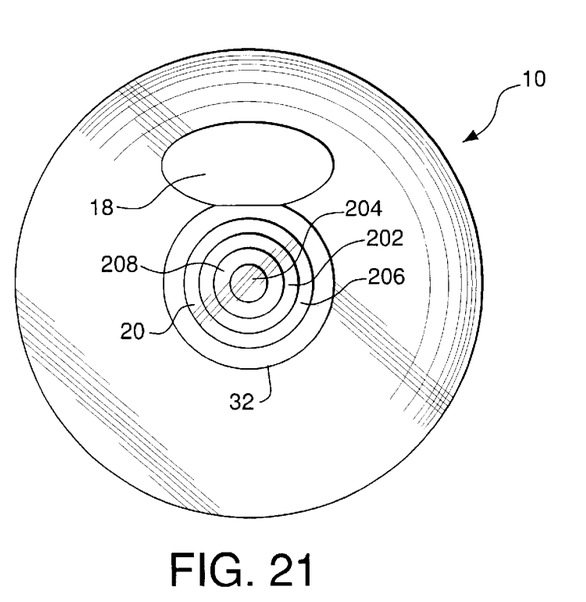
FIG. 21 is a front elevational view of the implant and eye of FIG. 20, taken along lines 21—21.

Flap 18 can then be repositioned over the exposed surface and the implant 120 in a relaxed state, as shown in FIG. 19, and similar to the repositioning of the flap described above.

The procedures for the myopia and hyperopia, described above and the descriptions of implants also described above are similar to those for the embodiment of FIGS. 15–18 and any description thereof is application for this embodiment.

Furthermore, the features of the of the embodiments shown in FIGS. 1–15, which are substantially similar to the embodiment shown in FIGS. 14–19 are identified with like reference numbers.

Embodiment of FIGS. 20–25

As shown in FIGS. 20–25, different portions or areas of the implants can be ablated to allow for near and far vision zones, or in other words bifocal vision or multifocal vision. As seen specifically in FIG. 20, implant 20 can be ablated in two ring or circular shaped areas 202 and 204. Preferably the ringed areas are ablated so that the areas are concentric with the main optical axis 31 of the eye; however, the ringed areas do not necessarily need to be concentric with the main optical axis and do not necessarily need to be rings. The ablated area may be on any portion of the implant desired that results in near and far zones, for example, one portion, such as a bottom portion of the implant may be ablated, while a second portion, such as the top portion, is not ablated, thus creating a bifocal or multifocal effect.

Figure 22:
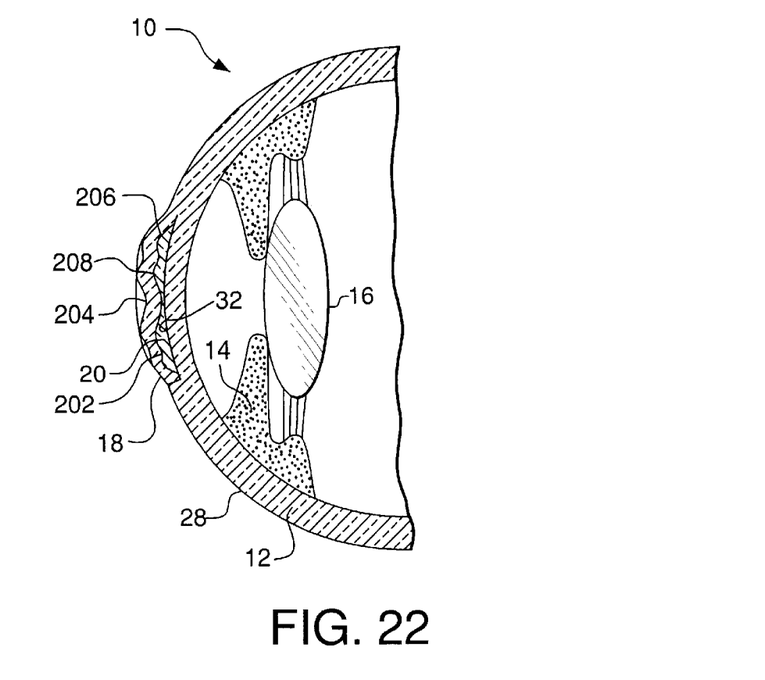
FIG. 22 is a side cross-sectional view of the implant and eye of FIG. 21 with the flap repositioned over the ablated implant.

The ablation of implant 20 in the preferred manner, that is substantially ring shaped, achieves a wave or W appearance in the cross section of the implant. Preferably, the implant 20 will have two zones 202 and 204 that will be ablated or adjusted for near vision and two zones 206 and 208 that are adjusted for far vision. However, it is noted that the implant may be ablated at any placed desired and in any number of places. For example, 1 or 3 or more ringed areas may be ablated and both the near and far area can be ablated to result in the desired change in the shape of the implant and therefore the cornea. As seen in FIG. 22, the cornea is then placed back over the implant in the same manner as described above for the other embodiments.

Figure 23:
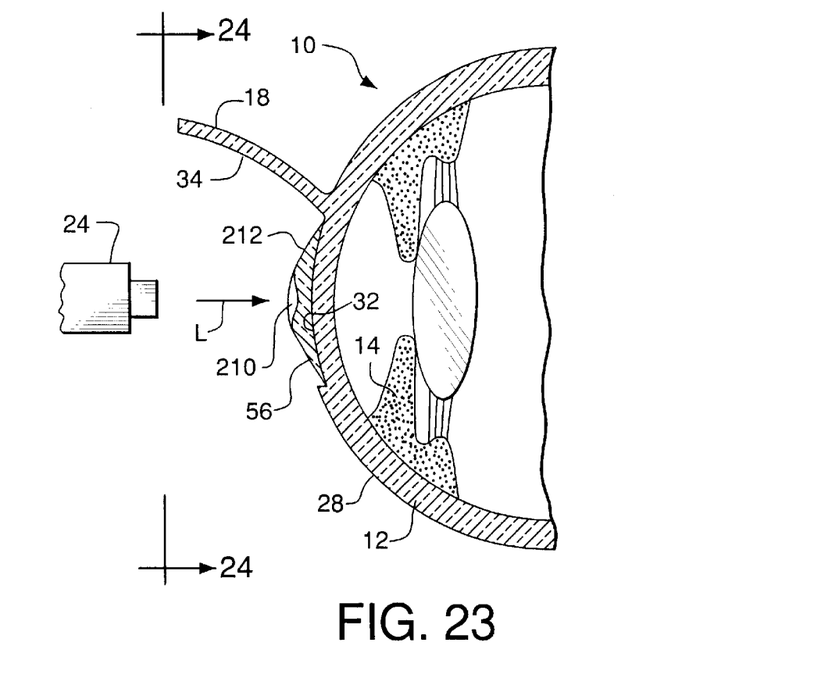
FIG. 23 is a side cross sectional view of the eye of FIG. 2 with the implant of FIG. 11 placed adjacent thereto and being laser ablated into separate zones for correction of near and far vision.
Figure 24:
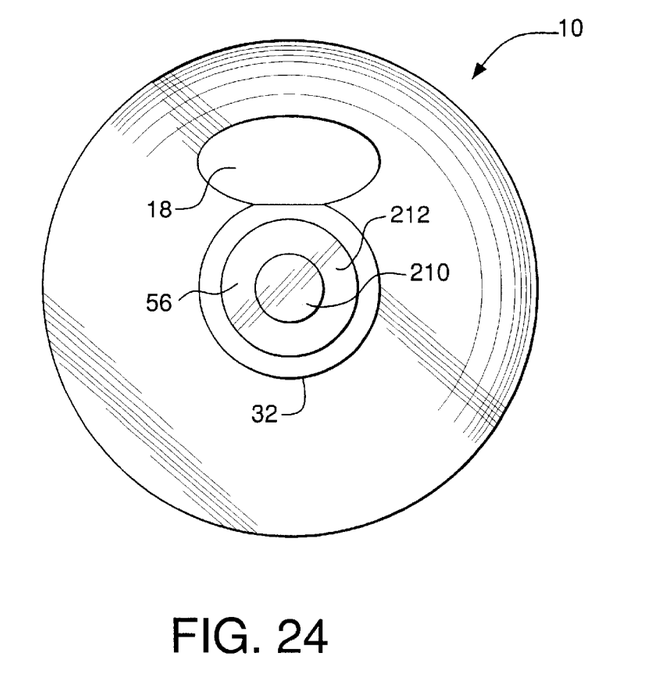
FIG. 24 is a front elevational view of the implant and eye of FIG. 23, taken along lines 23—23.
Figure 25:
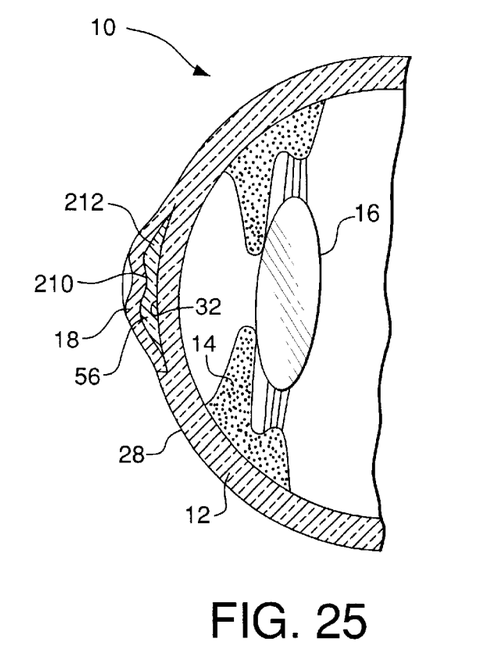
FIG. 25 is a side cross-sectional view of the implant and eye of FIG. 24 with the flap repositioned over the ablated implant.

Furthermore, as seen specifically in FIGS. 23–25 implant 56 can be ablated to form near zone 210 and far zone 212. As shown in FIG. 23, implant 56 is placed adjacent the exposed surface of the cornea and ablated in the desired areas, as described above, forming a recessed potion or near zone 210. Preferably, as seen in FIGS. 23 and 24, a central substantially circular area of the implant is ablated that is concentric with the main optical axis 31. However, as described above, the implant can be ablated in any place or manner and as often as desired to result in the proper number of near and/or far zones. As shown in FIG. 25, once the implant 56 is ablated, the cornea is repositioned over the implant, thus changing the refractive properties of the eye, as described above.

The procedures for the myopia and hyperopia, described above and the descriptions of implants also described above are similar to those for the embodiment of FIGS. 15–18 and any description thereof is application for this embodiment.

Furthermore, the features of the of the embodiments shown in FIGS. 1–15, which are substantially similar to the embodiment shown in FIGS. 20–25 are identified with like reference numbers.

While various advantageous embodiments have been chosen to illustrate the invention, it will be understood by those skilled in the art that various changes and modifications can be made therein without departing from the scope of the invention as defined in the appended claims.

What is claimed is:

1. A method of correcting the refractive error in a cornea of an eye, comprising the steps of
   forming a flap in the surface of the cornea,
   moving the flap to expose first and second internal surfaces of the cornea,
   positioning an implant adjacent the first internal surface, at least a portion of the implant having refractive properties,
   holding the implant adjacent the first internal surface using a tool,
   ablating at least a portion of said implant with a light emitting device, when said implant is positioned on said first exposed surface of said cornea and being held by said tool, and
   repositioning said flap over the implant.

2. A method according to claim 1, wherein
   the ablating step includes ablating a center portion of said implant.

3. A method according to claim 1, wherein
   the ablating step includes ablating a peripheral portion of said implant.

4. A method according to claim 1, wherein
   the positioning step includes positioning a concave implant on the first internal surface.

5. A method according to claim 4, wherein
   the ablating step includes ablating a center portion of said implant.

6. A method according to claim 1, further comprising the step of
   aiming said light emitting device at a marker on said implant; and
   ablating a portion of said implant that includes at least a portion of said marker.

7. A method according to claim 1, wherein
   the positioning step includes positioning a convex implant on the first internal surface.

8. A method according to claim 7, wherein
   the ablating step includes ablating a peripheral portion of said implant.

9. A method according to claim 1, further comprising
   using the tool to press the implant against the first internal surface of the cornea.

10. A method according to claim 9, wherein
    the using step includes using a substantially ring shape tool to press a peripheral portion of the implant against the first internal surface of the cornea.

11. A method according to claim 1, wherein
    said implant is between about 10–400 microns thick; and
    the ablating step includes ablating a portion no more than about 200 microns thick.

12. A method according to claim 1, wherein
    the ablating step includes ablating the at least a portion of the implant using an excimer laser.

13. A method according to claim 1, further comprising
    ablating at least one of said first and second internal surfaces of the cornea with a laser.

14. A method according to claim 1, wherein
    the ablating step includes ablating the at least a portion of the implant so that the ablated portion forms a substantially ring-shaped area concentric with a main optical axis of the eye.

15. A method of correcting refractive error in a cornea of an eye, comprising the steps of
    separating a portion of a surface of the cornea into first and second internal surfaces to form a corneal layer, the first surface facing in an anterior direction of the eye and the second surface facing in a posterior direction of the eye,
    moving the corneal layer to expose the first internal surface,
    positioning a lens on the first internal surface,
    holding the lens stationary relative to the first internal surface using an instrument,
    ablating at least a portion of the lens using a laser when said lens is being held by said instrument, and moving the corneal layer so that the second internal surface substantially overlies the lens.

16. A method according to claim 15, wherein the ablating step includes ablating the center portion of said lens.

17. A method according to claim 15, wherein the ablating step includes ablating the peripheral portion of said lens.

18. A method according to claim 15, wherein the positioning step includes positioning a concave lens on the first internal surface.

19. A method according to claim 18, wherein the ablating step includes ablating a center portion of said first internal surface.

20. A method according to claim 15, wherein the positioning step includes positioning a convex first internal surface on the first internal surface.

21. A method according to claim 20, wherein the ablating step includes ablating the peripheral portion of said first internal surface.

22. A method according to claim 15, wherein the holding step includes using a substantially ring shape instrument to press a peripheral portion of the lens against the first internal surface of the cornea.

23. A method according to claim 15, wherein said lens is between about 10–400 microns thick; and the ablating step includes ablating a portion no more than about 200 microns thick.

24. A method according to claim 15, wherein the ablating step includes ablating the at least a portion of the lens using an excimer laser.

25. A method according to claim 15, further comprising ablating at least one of said first and second internal surfaces of the cornea with a laser.

26. A method according to claim 15, wherein the ablating step includes ablating the at least a portion of the lens so that the ablated portion forms a substantially ring-shaped area concentric with a main optical axis of the eye.

27. An intracorneal lens for correcting refractive error of a cornea, comprising:

a first surface adapted to be positioned on an exposed surface of a cornea, at least a portion of said first surface having a curvature with a first predetermined radius;

a second surface, at least a portion of said second surface having a curvature with a second predetermined radius; and a refractive portion extending between said at least a portion of said first surface having a curvature with a first predetermined radius and said at least a portion of said second surface having a curvature with a second predetermined radius;

a portion of each of said first surface, said second surface and said refractive portion being adapted to be ablated by a light emitting device while being held on an exposed surface of an eye with an instrument.

28. An intracorneal lens according to claim 27, wherein said portion of each of said first surface, said second surface and said refractive portion that is adapted to be ablated is a center portion of each of said portion.

29. An intracorneal lens according to claim 27, wherein said portion of each of said first surface, said second surface and said refractive portion that is adapted to be ablated is a peripheral portion of each of said portion.

30. An intracorneal lens according to claim 27, wherein said lens is concave.

31. An intracorneal lens according to claim 30, wherein said portion of each of said first surface, said second surface and said refractive portion that is adapted to be ablated is a center portion of each of said portion.

32. An intracorneal lens according to claim 27, wherein said lens is convex.

33. An intracorneal lens according to claim 32, wherein said portion of each of said first surface, said second surface and said refractive portion that is adapted to be ablated is a peripheral portion of each of said portion.

34. An intracorneal lens according to claim 33, wherein the instrument is a substantially ring shape holding device that is adapted to press a peripheral portion of the lens against the exposed surface of the cornea.

35. An intracorneal lens according to claim 27, wherein said lens is between about 10–400 microns thick.

36. An intracorneal lens according to claim 27, wherein the instrument is a substantially ring shape holding device that is adapted to press a peripheral portion of the implant against the first internal surface of the cornea.

37. An intracorneal lens according to claim 36, wherein said lens is between about 10–400 microns thick.

* * * * *